(12) United States Patent
Benk et al.

(10) Patent No.: US 11,536,631 B2
(45) Date of Patent: Dec. 27, 2022

(54) FLUID ANALYSIS MODULE AND FLUID ANALYZER

(71) Applicant: ResuSciTec GmbH, Freiburg (DE)

(72) Inventors: Christoph Benk, Freiburg (DE); Juergen Grudke, Krefeld (DE); Rainer Feldbruegge, Muenster (DE); Michael Borchardt, Neuenkirchen (DE)

(73) Assignee: RESUSCITEC GMBH, Freiburg (DE)

( * ) Notice: Subject to any disclaimer, the term of this patent is extended or adjusted under 35 U.S.C. 154(b) by 429 days.

(21) Appl. No.: 16/628,947

(22) PCT Filed: Jul. 4, 2018

(86) PCT No.: PCT/EP2018/068078
§ 371 (c)(1),
(2) Date: Jan. 6, 2020

(87) PCT Pub. No.: WO2019/008026
PCT Pub. Date: Jan. 10, 2019

(65) Prior Publication Data
US 2020/0217760 A1 Jul. 9, 2020

(30) Foreign Application Priority Data
Jul. 7, 2017 (DE) ...................... 10 2017 211 693.5

(51) Int. Cl.
*G01N 1/14* (2006.01)
*A61B 5/15* (2006.01)
(Continued)

(52) U.S. Cl.
CPC .......... *G01N 1/14* (2013.01); *A61B 5/150221* (2013.01); *A61B 5/150229* (2013.01);
(Continued)

(58) Field of Classification Search
CPC ........ G01N 1/14; G01N 33/49; G01N 33/493; A61B 5/150221; A61B 5/150229;
(Continued)

(56) References Cited

U.S. PATENT DOCUMENTS

| 4,479,762 A | 10/1984 | Bilstad et al. |
| 5,062,774 A | 11/1991 | Kramer et al. |

(Continued)

FOREIGN PATENT DOCUMENTS

DE  10 2011 056 271 A1  6/2013

OTHER PUBLICATIONS

International Search Report for PCT/EP2018/068078, dated Oct. 12, 2018; English translation submitted herewith (5 pgs.).

*Primary Examiner* — Roy M Punnoose
(74) *Attorney, Agent, or Firm* — Fitch, Even, Tabin & Flannery LLP

(57) ABSTRACT

The invention relates to a fluid analysis module that comprises for blood analysis: a module housing with a fluid inlet port; at least one fluid sensor that is integrated within the module housing and comprises a sensor surface that is able to make a fluidic connection with the fluid inlet port; a chamber integrated within the module housing. The chamber can be brought into a fluidic connection with the sensor surface of the at least one fluid sensor. At least one first liquid reservoir attached within the chamber which is able to be brought into a fluidic connection with the sensor surface of the at least one fluid sensor; and at least one module housing surface, on which an elastic, fluid-tight separating wall that is embodied in membrane-like fashion is attached At least in portions, under a separating wall at least one fluidic functional configured as a flow valve and at least one fluidic functional element configured as a delivery pump is attached so that the fluidic functional elements are operable (Continued)

by local mechanical deformation of the separating wall: a) only deliver fluid from the fluid inlet port into the chamber via the sensor surface and b) only deliver a liquid housed in the liquid reservoir from the liquid reservoir into the chamber via the sensor surface.

19 Claims, 1 Drawing Sheet

(51) Int. Cl.
    *G01N 33/49*     (2006.01)
    *G01N 33/493*     (2006.01)
    *A61M 1/36*     (2006.01)

(52) U.S. Cl.
    CPC ....... *A61B 5/150992* (2013.01); *G01N 33/49* (2013.01); *G01N 33/493* (2013.01); *A61B 2560/0223* (2013.01); *A61M 1/3609* (2014.02)

(58) Field of Classification Search
    CPC ...... A61B 5/150992; A61B 2560/0223; A61B 5/145; A61M 1/3609
    See application file for complete search history.

(56) References Cited

U.S. PATENT DOCUMENTS

| | | |
|---|---|---|
| 5,114,580 A | 5/1992 | Ahmad et al. |
| 6,171,238 B1 | 1/2001 | Klimes et al. |
| 2010/0137778 A1* | 6/2010 | Kunjan ............. A61B 5/14535 |
| | | 604/6.15 |
| 2015/0258544 A1 | 9/2015 | Stern et al. |

* cited by examiner

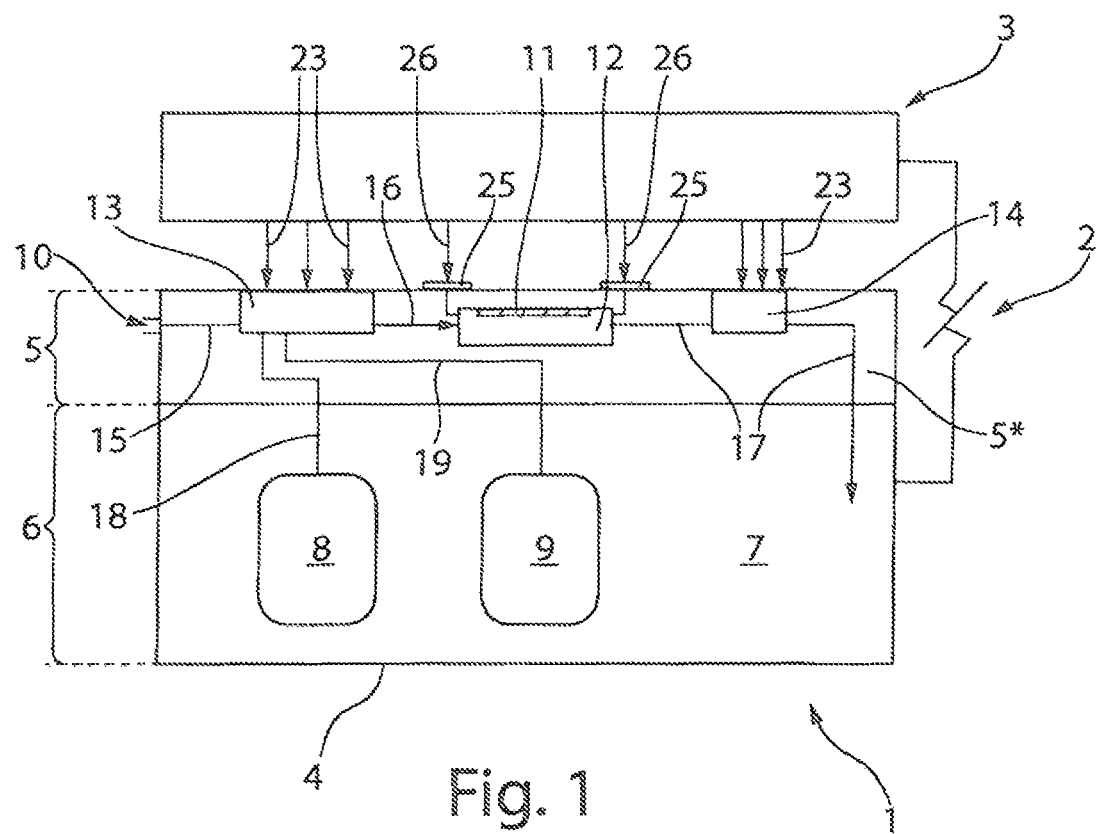
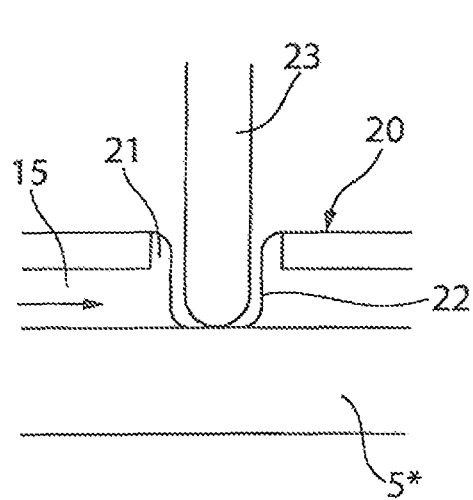
Fig. 2
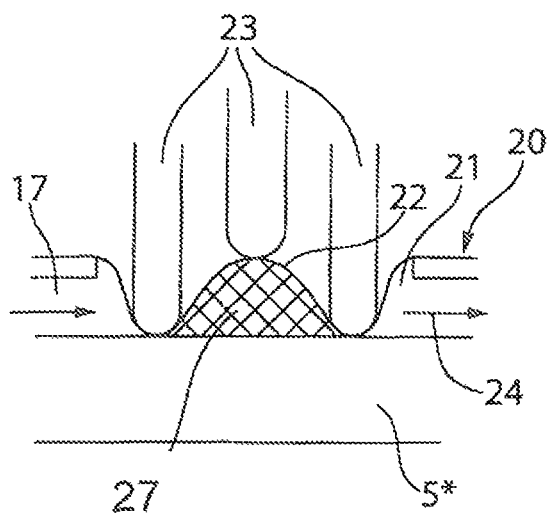
Fig. 3

FLUID ANALYSIS MODULE AND FLUID ANALYZER

CROSS REFERENCE TO RELATED APPLICATION

Reference is made to PCT/EP2018/068078 filed Jul. 4, 2018, designating the United States, which claims priority to German Application No. 10 2017 211 693.5 filed Jul. 7, 2017, which are incorporated herein by reference in their entirety

BACKGROUND OF THE INVENTION

Field of the Invention

The invention relates to a fluid analysis module which by use of a sensor detects fluids, in terms of the components thereof which in particular is for analysing biological liquids, preferably blood which has been taken as samples from a patient or which has to be analysed by way of an extracorporeal blood circulation system during a continuous measuring procedure.

Description of the Prior Art

A generic fluid analysis module is disclosed in DE 10 2011 056 271 A1, which is substantially composed of three plate-shaped functional units which are connected together, which are a carrier plate, fluidic card and a sensor card. Storage chambers and a receiving volume are contained inside the carrier plate with a sensor liquid for cleaning the sensor surface being housed therein. The fluidic card, which is attached directly via the carrier plate, is fluidically connected to receiving volumes present inside the carrier plate. The fluidic card contains fluid channels in which valves and pumps are arranged. The fluids housed in the carrier plate and also a body fluid supplied via a specific inlet are able to be delivered along specifically predeterminable fluid channels. The sensor card which is provided with sensors, terminates the fluid channels contained in the fluidic card on one side in a fluid-tight manner and directly contacts the liquids guided inside the fluid channels. Remote from the fluid channels, the sensor card comprises sensor contacts which come into electrical contact with a measuring module with the fluid analysis module be coupled thereto in a releasable and fixed manner.

A portable hand-held device comprising a biosensor is disclosed in U.S. Pat. No. 6,171,238, which provides an amperometric biosensor inside a measuring cell to which a cleaning liquid, which is housed in a storage bag, and a fluid sample, which may be supplied via a sample opening, may be supplied via a tube transport system as required. All fluids flowing through the measuring cell pass into a correspondingly provided waste bag. The portable hand-held device has an evaluation, display and energy storage unit whereby autonomous operation is possible.

U.S. Pat. No. 4,479,762 discloses a module for carrying out a plasmapheresis, in which blood from a donor is delivered into the module, in which blood plasma is separated out from the donor blood and the red blood cells remaining in the blood are returned again to the donor. The module has a fluid line system with liquid reservoirs. The fluid line system may releasable contact, via a fluid-tight elastic separating membrane with an external actuator system which initiates a fluid flow inside the fluid line system by the action of pulsating pressure.

U.S. Pat. No. 5,062,774 discloses a fluid pump system to which liquid containers are connectable thereto. The fluid pump system is able to produce any liquid mixtures from the individual liquids.

All known fluid analysis modules, however, have the drawback that they constitute technically sophisticated and thus cost-intensive functional units due to their complexity and optimal miniaturized integration of a plurality of different functional components. In particular, with regard to the medical-biological use of such fluid analysis modules for examining a large number of different measuring samples, such as for example blood samples from different people, such fluid analysis modules are frequently configured as single-use articles, so-called disposable articles, in order to avoid cross contamination.

SUMMARY OF THE INVENTION

The invention is configurable fluid analysis device of the aforementioned generic type in a design which is as complex as possible and which has a construction which is as small as possible. Substantially all components for the supply, measurement and disposal of the respective fluids are designed to be contained therein and are designed to be configured to be as cost-effective as possible and suitable for easy disposal, that is without any electronic components.

The fluid analysis module according to the invention is configured as a single structural unit which provides a module housing which has one, which is preferably a single fluid inlet port. At least one fluid sensor is integrated within the module housing and comprises a sensor surface that is able to have a fluidic connection with the fluid inlet port. Moreover, a chamber is arranged within the module housing, which may be placed into a fluidic connection with the sensor surface of the at least one fluid sensor. At least one first liquid reservoir is attached within the chamber, which may be brought into a fluidic connection with the sensor surface of the at least one fluid sensor. The module housing also has at least one module housing surface, on which an elastic fluid-tight separating wall, that is embodied as a membrane is attached, at least in portions, under which the separating wall has at least one fluidic functional element which is a flow valve and at least one fluidic functional element which is a delivery pump are attached and are operable in at least one of the following ways only resulting from local mechanical deformation of the separating wall:
  only delivering fluid from the fluid inlet port into the chamber while contacting the sensor surface, and
  only delivering a liquid housed in the at least one liquid reservoir from the liquid reservoir into the chamber while contacting the sensor surface.

Preferably, at least one second liquid reservoir is attached inside the chamber. The second liquid reservoir may make a fluidic connection with the sensor surface of the at least one fluid sensor by at least one of two fluidic functional elements and at least one additional fluidic functional element which is a flow valve or a delivery pump. In particular, for the purpose of the analysis of biological fluids, primarily blood, it is necessary to clean and to calibrate the sensor surface before a blood measurement is carried out. Thus a sensor flushing liquid or calibration liquid is located in a first liquid reservoir accommodated inside the chamber and a calibration liquid is located in a second liquid reservoir accommodated inside the chamber.

Since the chamber additionally serves as at least one of a collection volume and a disposal volume both for the fluid to be measured, for example blood, and also for the liquid housed in the at least one liquid reservoir accommodated inside the chamber, the at least one liquid reservoir is configured as a fluid-tight elastic bag. When the at least one bag is emptied, the bag volume decreases and at the same time the receiving volume for the fluids to be disposed of increases inside the chamber, which otherwise has a constant chamber volume.

The module housing is able to be subdivided into a measuring carrier and a chamber region. That is the measuring carrier is positioned permanently on the chamber and defines the chamber at least on one side. In this case, the measuring carrier has an upper face which is remote from the chamber and the elastic fluid-tight separating wall is a membrane attached thereto, at least in portions.

The fluid inlet port is first attached in the region of the measuring carrier and inside the measuring carrier at least one fluid line is fluidically connected to the sensor surface of the at least one fluid sensor and at least one fluid line leading therefrom inside the measuring carrier and discharging into the chamber. In order to control the fluid flow between the fluid inlet port, the sensor surface and the chamber, first at least one fluidic functional element in the style of a flow valve is arranged along at least one of the fluid lines, secondly the fluid lines are able to be brought into a fluidic operative connection with the at least one fluidic functional element which is a delivery pump.

For the purposes of the required cleaning or calibration of the sensor surface, the at least one liquid reservoir is fluidically connected to the sensor surface of the at least one fluid sensor via a fluid line which discharges into the region of the measuring carrier, at least one fluid line leading away from the fluid sensor inside the measuring carrier and discharges into the chamber. Also in this case, at least one fluidic functional element which is a flow valve is arranged along at least one of the fluid lines, which are connectable into a fluidic operative connection with the at least one fluidic functional element which is a delivery pump.

The at least one fluidic functional element is a flow valve configured in a fluid channel portion that opens toward the module housing surface which is spanned by the elastic fluid-tight separating wall that is a membrane. For the purposes of at least one of valve actuation and valve control, a local deformation of the separating wall by the application of force is required, such that the fluid channel portion is sealed locally in a fluid-tight manner by the locally deformed separating wall. Preferably an external actuator positioned along an adjusting path, which is attached adjacent to the separating wall, deforms the separating wall locally.

The at least one fluidic functional element which is a delivery pump configured in a fluid channel portion which is open toward the module housing surface which is spanned by the elastic fluid-tight separating wall that is a membrane. For the purposes of pump activation, a local deformation of the separating wall by the application of force is required, such that the fluid channel portion indirectly or directly encloses the locally deformed separating wall to deliver volumes moving forward in a peristaltic manner in a fluid channel direction, similar to the principle of a peristaltic pump.

Additionally, at least two freely accessible electrode surfaces are attached to the at least one module housing surface which are electrically connected to the at least one fluid sensor.

A control and evaluation unit is required both for the mechanical activation of the fluidic functional elements and also for the electrical contact of the at least one fluid sensor inside the fluid analysis module. The control and evaluation unit are able to be coupled to the fluid analysis module in a releasable and fixed manner and mechanical actuating elements being provided by the control and evaluation unit that are able to engage the fluidic functional elements via the elastic fluid-tight separating wall that is a membrane. Moreover, an electrical connection is produced between the control and evaluation unit and the at least one fluid sensor via the at least two electrode surfaces which are freely attached to the module housing surface.

The fluid analyzer, which is the fluid analysis module and the control and evaluation unit, are advantageously all electronic components, which are not in contact with the fluid to be measured by a sensor and are controlled by the control and evaluation unit. However, the fluid analysis module as a whole is all mechanical components and, in particular, in the case of a suitable configuration of the fluid sensor contains no electronic components.

The fluid analyzer is advantageously suitable for the analysis of biological fluids, for example blood, liquor, serum and urine, by use of a sensor. For this intended purpose, a liquid reservoir with a flushing liquid or calibration liquid and a further liquid reservoir with a calibration liquid for the sensor surface are contained inside the chamber.

BRIEF DESCRIPTION OF THE DRAWINGS

The invention is described by way of example hereinafter without limitation of an exemplary embodiment with reference to the drawings, in which:

FIG. 1 shows a schematic structure of a fluid analysis module configured according to the invention with the control and evaluation unit coupled thereto;

FIG. 2 shows an illustration of a fluidic functional element configured to be a flow valve; and FIG. 3 shows an illustration of a fluidic functional element configured to be a delivery pump.

DETAILED DESCRIPTION OF THE INVENTION

FIG. 1 shows a schematic structure of a fluid analysis module 1 which is mechanically coupled to a control and evaluation unit 3 via a mechanically releasable interface 2. The fluid analysis module 1 in combination with the control and evaluation unit 3 forms a fluid analyzer.

The fluid module 1 shown in FIG. 1 is surrounded by a module housing 4 and thus constitutes a single unit which may be operated as a single unit. The fluid analysis module 1 is able to be functionally subdivided into a measuring carrier region 5 and a chamber region 6. The chamber region 6 has a chamber 7 in which two liquid reservoirs 8, 9 which are elastic bags, are incorporated. The bag-shaped liquid reservoirs 8, 9, with the exception of the fluid lines discharging into the measuring carrier region 5, are otherwise loosely mounted inside the chamber 7.

The measuring carrier 5* has a fluid inlet port 10, via which a liquid to be analysed by at least one of a sensor and a fluid to be analysed by use of a sensor, for example blood, is able to be fed into the measuring carrier 5*. Inside the measuring carrier 5* is located at least one fluid sensor 12 which has at least one sensor surface 11 via which the fluid to be examined by the at least one fluid sensor is guided inside the fluid sensor 12.

The fluid entering the measuring carrier 5* via the fluid inlet port 10 is guided into the fluid sensor 12 via the fluid lines 15, 16. Leading away from the fluid sensor 12 is a fluid line 17 which is provided inside the measuring carrier 5*, via which fluid flowing through the fluid sensor 12 directly discharges into the volume of the chamber 7 which serves as at least one of a fluid collection and disposal chamber.

In order to ensure a flow in a defined manner along the fluid lines 15, 16 and 17, fluidic functional elements 13 and 14 are provided inside the measuring carrier 5*. The fluidic functional element 13, which is provided in FIG. 1 between the fluid line 15 and 16, is a valve permitting selective closing and opening of the connection between the fluid lines 15 and 16. The fluidic functional element 14, which is provided along the fluid line 17, is a delivery pump which ensures a controlled flow along the respective fluid lines. Depending on the design, the fluidic functional elements 13, 14 may be attached to regions along the fluid lines which differ from those shown in the figures.

For the purpose of cleaning or calibrating the sensor surface 11 of the fluid sensor 12, flushing liquid or calibration liquid is guided from the fluid reservoir 8, which stores a flushing liquid or calibration liquid, to the fluid sensor 12 via the fluid lines 16 and 18, which is ultimately disposed of again via the fluid line 17 into the chamber 7. To this end, the valve control of the fluidic functional element 13 has to be performed, such that it is ensured that the supply along the fluid line is closed 15 and only the fluid lines 18 and 16 are fluidically connected.

For the purposes of calibrating the sensor, a calibration liquid is housed inside the fluid reservoir 9. The calibration liquid passes to the fluid sensor 12 via the fluid lines 19 and 16 and is transferred therefrom via the fluid line 17 into the collection volume of the chamber 7. Also in this case, it is necessary to perform the valve control of the fluidic functional element 13, with the fluid lines 15 and 18 being closed, while the fluid line 19 for a supply of calibration liquid to the fluid sensor 12 is open.

In FIG. 2 a cross section through a fluidic functional element which is a valve 13 is illustrated. Thus, for example, the fluid line 15 shown in FIG. 2 has a recess 21 which is configured to be open toward the module housing surface 20 and which is spanned by an elastic fluid-tight separating wall 22 that is embodied as a membrane. If it is necessary to close the flow path along the fluid channel 15, a deformation of the separating wall 22 by the application of force is required, such that the separating wall ensures a local fluid-tight seal inside the fluid line 15. Advantageously, an actuating element 23, which is attached to the sides of the control and evaluation unit 3, is used.

In each case a fluidic functional element configured as a value according to FIG. 2 is provided at least along each of the fluid channels 15, 18 and 19 shown in FIG. 1.

FIG. 3 illustrates a possible embodiment for implementing a fluidic functional element as a delivery pump. The fluid channel 17 has a recess 21 which is oriented toward the module housing surface 20 and which is spanned by an elastic fluid-tight separating wall 22 that is a membrane. For the purpose of implementing a fluid flow in the delivery direction 24 at least three actuating elements 23, with actuating strokes respectively adapted to one another and which are attached to the sides of the control and evaluation unit 3, contact the separating wall 22 which has to be deformed such that it encloses with the fluid channel wall a delivered volume 27 which moves forward in a peristaltic manner in the delivery direction 24.

Finally, at least two electrode surfaces 25 are attached to the module housing surface 20 so that the fluid sensor signals are able to be picked up thereby. To this end, the control and evaluation unit 3 has corresponding electrode contacts 26.

The fluid analysis module 1 according to the invention uses components which are simple and cost-effective to produce and is suitable, in particular, as at least one of a single-use article and disposable article. Since the fluid analysis module 1 contains no electrical components, disposal is easy. All actuators and electronic components are attached to the control and evaluation unit 3 and are exclusively brought into an operative connection with the fluid analyzer via a fluid-tight separating wall so that the control and evaluation unit is not subjected to any contamination during at least one of a measuring process and measuring cycle.

LIST OF REFERENCE NUMERALS

1 Fluid analysis module
2 Mechanical interface
3 Control and evaluation unit
4 Module housing
5 Measuring carrier region
6 Chamber region
7 Chamber
8 First fluid reservoir
9 Second fluid reservoir
10 Fluid inlet port
11 Sensor surface
12 Fluid sensor
13 Fluidic functional element configured as a flow valve
14 Fluidic functional element configured as a delivery pump
15, 16, 17, 18, 19 Fluid lines
20 Module housing surface
21 Recess
22 Separating wall
23 Actuating element
24 Delivery direction
25 Electrode surfaces
26 Electrode contacts
27 Delivered volumes

The invention claimed is:

1. A fluid analysis module comprising:
   a module housing including a fluid inlet port;
   at least one fluid sensor integrated within the module housing and comprising a sensor surface that is brought into a fluidic connection with the fluid inlet port;
   a chamber integrated within the module housing, the chamber being configured to be brought into a fluidic connection with a sensor surface of the at least one fluid sensor;
   at least one first liquid reservoir attached within the chamber, the liquid reservoir being configured to be brought into a fluidic connection with the sensor surface of the at least one fluid sensor; and
   at least one module housing surface on which an elastic fluid-tight separating wall is located which provides a membrane which has at least a portion under the separating wall which is at least moveable functionally as a flow valve and at least one delivery pump which operates only by mechanical deformation of the separating wall to deliver only fluid from the fluid inlet port into the chamber via the sensor surface and which delivers only a liquid housed in the at least one liquid reservoir into the chamber via the sensor surface.

2. The fluid analysis module according to claim 1, comprising:

at least one second liquid reservoir attached inside the chamber, the at least one second liquid reservoir being brought into a fluidic connection with the sensor surface of the at least one fluid sensor by a flow valve or a delivery pump.

3. The fluid analysis module according to claim 2, wherein:
the at least one liquid reservoir comprises a fluid-tight elastic bag.

4. The fluid analyzer module according to claim 3, comprising:
a control and evaluation unit, the fluid analysis module is configured to be releasable and fixed so that mechanical actuating elements of the control and evaluation unit are brought into engagement with the fluidic functional elements via the elastic fluid-tight separating wall, and an electrical connection extending between the control and evaluation unit and the at least one fluid sensor via at least two electrode surfaces is attached to the module housing surface.

5. The fluid analyzer module according to claim 2, comprising:
a control and evaluation unit, the fluid analysis module is configured to be releasable and fixed so that mechanical actuating elements of the control and evaluation unit are brought into engagement with the fluidic functional elements via the elastic fluid-tight separating wall, and an electrical connection extending between the control and evaluation unit and the at least one fluid sensor via at least two electrode surfaces is attached to the module housing surface.

6. The fluid analysis module according to claim 1, wherein:
the at least one liquid reservoir comprises a fluid-tight elastic bag.

7. The fluid analyzer module according to claim 6, comprising:
a control and evaluation unit, the fluid analysis module is configured to be releasable and fixed so that mechanical actuating elements of the control and evaluation unit are brought into engagement with the fluidic functional elements via the elastic fluid-tight separating wall, and an electrical connection extending between the control and evaluation unit and the at least one fluid sensor via at least two electrode surfaces is attached to the module housing surface.

8. The fluid analysis module according to claim 1, comprising:
the module housing is subdivided into a measuring carrier and a chamber region, with the measuring carrier positioned on the chamber and defining the chamber at least on one side and the measuring carrier has an upper face remote from the chamber and the elastic fluid-tight separating wall is a membrane attached at least to the portion.

9. The fluid analysis module according to claim 8, wherein:
the fluid inlet port is attached to an inside part of the measuring carrier along at least one fluid line fluidically connected to the sensor surface of the at least one fluid sensor, at least one fluid line extends inside the measuring carrier and discharges fluid into the chamber, the flow valve is positioned along at least one of the fluid lines, and one of the fluid lines connects into a fluidic operative connection with the delivery pump.

10. The fluid analysis module according to claim 8, wherein:

the at least one liquid reservoir is fluidically connected to the sensor surface of the at least one fluid sensor via a discharge fluid line which discharges fluid into a part of the measuring carrier, at least one leading fluid line leads away from the fluid sensor inside the measuring carrier and discharges into the chamber, and the flow valve is positioned along at least one of the fluid lines, and the discharge fluid line and the leading fluid line are connectable into a fluidic operative connection with the delivery pump.

11. The fluid analysis module according to claim 10, wherein:
the at least one liquid reservoir is fluidically connected to the sensor surface of the at least one fluid sensor via a discharge fluid line which discharges fluid into a part of the measuring carrier, at least one leading fluid line leads away from the fluid sensor inside the measuring carrier and discharges into the chamber, and the flow valve is positioned along at least one of the fluid lines, and the discharge fluid line and the leading fluid line are connectable into a fluidic operative connection with the delivery pump.

12. The fluid analysis module according to claim 1, comprising:
at least two accessible electrode surfaces attached to at least one module housing surface which are electrically connected to the at least one fluid sensor.

13. The fluid analysis module according to claim 12, wherein:
the flow valve comprises a fluid channel portion opening toward the module housing surface which is spanned by the elastic fluid-tight separating wall that is a membrane, and the elastic fluid-tight separating wall is deformable by application of force thereto so that the fluid channel portion is sealed by a deformed elastic fluid-tight separating wall.

14. The fluid analysis module according to claim 13, wherein:
the delivery pump comprises a fluid channel opening toward the at least one module housing surface by the elastic fluid-tight separating wall, and the separating wall is deformable by the application of force so that the fluid channel is enclosed with the deformed fluid-tight separating wall to deliver volumes of fluid moving forward peristaltically in a direction of the fluid channel.

15. The fluid analyzer module according to claim 1, comprising:
a control and evaluation unit, the fluid analysis module is configured to be releasable and fixed so that mechanical actuating elements of the control and evaluation unit are brought into engagement with the fluidic functional elements via the elastic fluid-tight separating wall, and an electrical connection extending between the control and evaluation unit and the at least one fluid sensor via at least two electrode surfaces is attached to the module housing surface.

16. In a fluid analysis module comprising a module housing including a fluid inlet port at least one fluid sensor integrated within the module housing and comprising a sensor surface that is brought into a fluidic connection with the fluid inlet port, a chamber integrated within the module housing, the chamber being configured to be brought into a fluidic connection with a sensor surface of the at least one fluid sensor, at least one first liquid reservoir attached within the chamber, the liquid reservoir being configured to be brought into a fluidic connection with the sensor surface of the at least one fluid sensor, and at least one module housing surface on which an elastic fluid-tight separating wall is located which provides a membrane which has at least a portion under the separating wall that is moveable to function as a flow valve and at least one delivery pump which operates only by mechanical deformation of the separating wall to deliver only fluid from the fluid inlet port into the chamber via the sensor surface and which delivers only a liquid housed in the at least one liquid reservoir from the liquid reservoir into the chamber via the sensor surface, a method comprising:

using the fluid analysis module to analyze biological fluids comprising blood, liquid, serum, urine or reperfusate.

17. In a fluid analysis module comprising a module housing including a fluid inlet port, at least one fluid sensor integrated within the module housing and comprising a sensor surface that is brought into a fluidic connection with the fluid inlet port, a chamber integrated within the module housing, the chamber being configured to be brought into a fluidic connection with a sensor surface of the at least one fluid sensor, at least one first liquid reservoir attached within the chamber, the liquid reservoir being configured to be brought into a fluidic connection with the sensor surface of the at least one fluid sensor, and at least one module housing surface, on which an elastic fluid-tight separating wall is located which provides a membrane which has at least portions under the separating wall that is moveable to function as a flow valve and at least one delivery pump which operates only by mechanical deformation of the separating wall to deliver only fluid from the fluid inlet port into the chamber via the sensor surface and which delivers only a liquid housed in the at least one liquid reservoir from the liquid reservoir into the chamber via the sensor surface, at least one second liquid reservoir is attached inside the chamber, a method comprising:

a second liquid reservoir in a fluidic connection with the sensor surface of the at least one fluid sensor and the membrane functioning as a flow valve or as delivery pump.

18. A method in accordance with claim 17, wherein:
the at least one first liquid reservoir comprises a fluid-tight bag.

19. A method in accordance with claim 17, wherein:
the at least one first liquid reservoir provides a flushing liquid or a calibration liquid which are located inside the chamber.

\* \* \* \* \*